(12) United States Patent
Harosh

(10) Patent No.: US 6,210,888 B1
(45) Date of Patent: Apr. 3, 2001

(54) TECHNIQUE FOR SCREENING INHIBITORS OF DEAMINATION ENZYME ACTIVITY

(76) Inventor: Itzik Harosh, 25240 Moshav, Ben-Ami (IL)

(*) Notice: Subject to any disclaimer, the term of this patent is extended or adjusted under 35 U.S.C. 154(b) by 0 days.

(21) Appl. No.: 09/208,378

(22) Filed: Dec. 10, 1998

(51) Int. Cl.[7] .............................. C12Q 1/68; C07H 19/00
(52) U.S. Cl. .................. 435/6; 435/69; 435/91.1; 536/22.1; 536/23.1; 536/23.2; 536/23.5
(58) Field of Search ............... 435/6, 91.1, 69.1; 536/22.1, 23.1, 23.2, 23.5

(56) References Cited

U.S. PATENT DOCUMENTS 5,434,058 * 7/1995 Davidson ..................... 435/69.1

OTHER PUBLICATIONS

Davies et al, "Sequence Requirements for Apolipoprotein B RNA Editing in Transfected Rat Hepatoma Cells", *J. Biological Chemistry*, 264(23):13395–13398, 1989.

Vincenzetti et al, "Recombinant Human Cytidine Deaminase: Expression, Purification, and Characterization", *Protein Expression and Purification*, 8(2): 247–253, 1996 found in *Biological Abstracts*,102(10): Abstr. No. 146673, 1996.

Stratagene Catalog p. 39, 1988.*

* cited by examiner

Primary Examiner—Jezia Riley

(57) ABSTRACT

The invention concerns a technique for the sensitive, efficient and quick screening of molecules capable of inhibiting the deaminase activity of an enzyme at a cytidine or a 5-methylated cytosine in RNA or DNA.

7 Claims, 2 Drawing Sheets

TECHNIQUE FOR SCREENING INHIBITORS OF DEAMINATION ENZYME ACTIVITY

Figure 1:
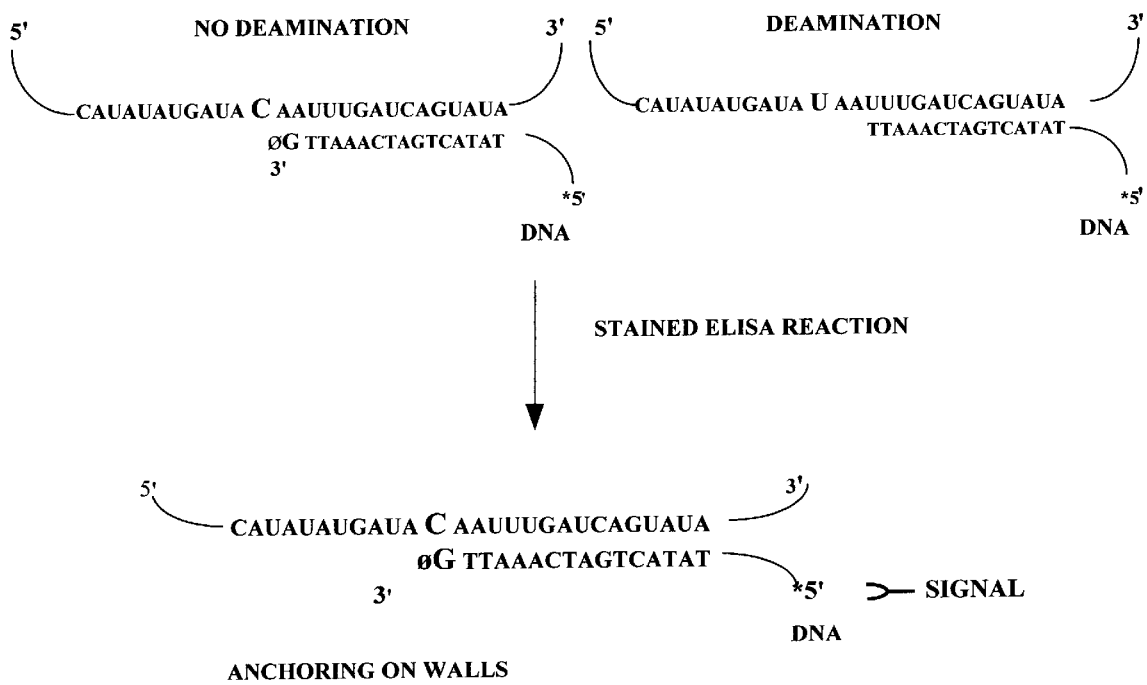

The present invention discloses a technique for detecting deamination of a cytidine in RNAs or DNAs (for example a single strand mRNA, or a double strand viral RNA etc.). This technique is based on knowledge of the local sequence of the RNA or DNA containing the deaminated site. This sequence is used to produce a primer oligonucleotide (DNA or RNA) just at 3' of the deaminated site (stopping at 3' of the deaminated site at a site such that the intermediate sequence only comprises one, two or three types of nucleotides). This primer is labelled for example at terminal 5' or in its proximity, in particular through incorporation of modified nucleotides (biotinilated, radiolabelled, fluorescent etc.) or by chemical modification of this terminal such that said terminal may be detected by chemical, biochemical or other reaction in particular with a substrate, or by fluorescence, radioactivity detection etc. One example of said system of detection is given by the SPA® system (Scintillation Proximity Assay) coupled to DNA primers, commercially available from Amersham.

This primer is hybridised with the RNA or DNA to be assayed in the presence of Reverse Transcriptase (for RNA/DNA hybridisation), of RNA polymerase (for RNA/RNA hybridisation), or of DNA polymerase (for DNA/DNA hybridisation) and modified adenine. If the site to be assayed is deaminated (normal case: non-deaminated), one to three nucleotides are added to each pricer hybridised to a deaminated RNA or DNA. Conversely, to detect the absence of deamination of a site (normal case: deaminated), modified quanine is used (for example biotinilated, radiolabelled, fluorescent etc.).

After extending the primers they are denatured and placed in the presence of an exposure system, either modified nucleotides to be incorporated, or primer terminals so as to detect and/or quantify the incorporation of the modified nucleotides.

One example of embodiment of this system entails a primer containing one or more nucleotides digoxygenated at its 5' terminal or in its proximity, in which the incorporated nucleotides is biotinilated. After incorporation, the incorporated primer+nucleotide unit (extended primer) is trapped in a well treated with streptavidine, which is rinsed to remove non-extended primers, and exposed using a standard ELISA technique (see FIG. 1). The symmetric system in which the incorporated nucleotide is digoxygenated, and the biotinilated 5' terminal can be used just as advantageously. It is also possible, instead of labelling for example the 5' terminal of the primer used, to label the DNA or RNA being assayed which contains the nucleotide likely to be deaminated (see FIG. 2).

The present invention also relates to a technique which can be used to detect the deamination of methylated cytidine (5mC) in RNAs or DNAs. This technique is based upon knowledge of the local sequence of the RNA or DNA containing the deaminated site. This sequence is used to produce a primer oligonucleotide (DNA or RNA) just at 3' of the deaminated site (stopping at 3' of the deaminated site, at a site such that the intermediate sequence only comprises one, two or three types of nucleotides (see FIG. 1). This primer is labelled for example at the 5' terminal or in its proximity, in particular through incorporation of one to three modified nucleotides (biotinilated, radiolabelled, fluorescent etc.) or by chemical modification of the terminal, such that said terminal may be detected by chemical, biochemical or other reaction, in particular with a substrate, or by fluorescence, radioactivity detection etc. One example of said detection system has already been cited previously.

This primer is hybridised to the RNA or DNA to be assayed in the presence of Reverse Transcriptase (for RNA/DNA hybridisation), of RNA polymerase (for RNA/RNA hybridisation), or of DNA polymerase (for DNA/DNA hybridisation) and modified adenine. If the site to be studies is deaminated (normal case: non-deaminated), one nucleotide (at least) is added to each hybridised primer. Conversely, to detect the absence of deamination of a site (normal case: deaminated), modified quanine is used (for example biotinilated, radiolabelled, fluorescent etc.).

After extending the primers they are denatured and placed in the presence of a an exposure system, either modified nucleotides to be incorporated, or primer terminals so as to detect and/or quantify the incorporation of the modified nucleotides.

One example of embodiment of this system entails a primer containing one or more nucleotides digoxygenated at its 5' terminal or in its proximity, in which the incorporated nucleotide is biotinilated. After incorporation, the incorporated primer+nucleotide unit (extended primer) is trapped in a well treated with streptavidine, which is rinsed to remove non-extended primers, and exposed using a standard ELISA technique (see FIG. 1). The symmetric system in which the incorporated nucleotide is digoxygenated, and the biotinilated 5' terminal can be used just as advantageously. It is also possible, instead of labelling for example terminal 5' of the primer used, to label the DNA or RNA being assayed containing the nucleotide likely to be deaminated.

This invention concerns a RNA or DNA deamination detection kit containing at least one of the following elements:

a) a labelled RNA or DNA primer b) one to three labelled nucleotides c) the reagents and mediums required to extend the primer d) a system for detecting the incorporation of the labelled nucleotides.

The present invention discloses a quick method for screening molecules having an inhibitory effect on the deaminase activity of an enzyme acting on a specific RNA (respectively a DNA) and a device for its implementation: This method (see FIGS 1 and 2) consists of using a RNA (or DNA respectively) substrate containing the minimum sequence around the deaminated cytosine required for the observation of normal activity of the deaminase enzyme. To this substrate is added a crude extract of cell proteins in which this activity takes place, DNA (or RNA) primers allowing the implementation of the technique described previously for the detection of deamination of a cytosine in an RNA (respectively DNA) of the assayed cytosine, and modified nucleotides (adenine for the detection of deamination, quanine for the detection of non-deamination), plus one or more molecules or products whose inhibitory effect is to be assayed.

The present invention also relates to all molecules or products having an inhibitory effect on said enzyme or associated proteins, discovered by one of the techniques described in this invention.

This invention applies in particular to the screening of molecules inhibiting the deamination activity of apobec-1, or the activity of associated proteins (Shah R R et al (1991) J. Biol. Chem. 16301–16304, Davies M S et al (1989) J. Biol. Chem. 13395–13398), which may have therapeutic use in atherosclerosis and obesity and other diseases characterized by a higher than normal plasma level of chylomicrons and/or VLDL (hyperlipidaemia, for example hypercholesterosaemia, hypertriglyceridaemia etc.) and/or by hyperglycaemia.

The deaminated cytidine being assayed here is the cytidine at position 6666 of the mRNA of apoB, the RNA sequence used as substrate containing the anchor zone of apobec-1 or of the associated proteins is that described in the literature (Shah R R et al (1991) J. Biol. Chem. 16301–16304, Davies M S et al (1989) J. Biol. Chem. 13395–13398) (called anchor sequence of the mRNA of apoB), and the protein extracts used may be derived from rat livers or other sources. The sequence used a primer for the implementation of the technique contains a number of complementary nucleotides of the 3' sequence of site 6666 of the mRNA of apoB that is sufficient for proper hybridisation (at least 14 nucleotides).

This invention therefore concerns a technique for detecting the deamination of cytidine at position 6666 of the mRNA of apoB as previously described, and a kit for detecting RNA deamination comprising the anchor sequence of the mRNA of apoB, which contains at least one of the following elements:

a) a labelled RNA or DNA primer
b) one to three labelled nucleotides
c) the reagents and media required to extend the primer
d) a system for detecting the incorporation of the labelled nucleotides The present invention also discloses a quick method for screening molecules having an inhibitory effect on the deaminase activity of apobec-1, based on the detection technique of specific deamination of RNA described previously, in which a RNA substrate is used containing the anchor sequence of the mRNA of apoB. To this substrate is added a crude extract of cell proteins in which this activity takes place, DNA (or RNA) primers used to implement the previously described technique for detecting the deamination of a cytidine in an RNA for the cytidine being assayed, and modified nucleotides (adenine for the detection of deamination, quanine for the detection of non-deamination), plus one or more molecules or products whose inhibitory effect is to be assayed on the deaminase activity of apobec-1.

The present invention relates to all the molecules or products having an inhibitory effect on the deaminase activity of apobec-1, or of associated proteins, discovered by one or more of the techniques described in this invention.

KEYS TO FIGURES

FIG. 1 Screening inhibitors of the deaminase activity of an enzyme using a technique for detecting deamination. Example of apobec-1 and technique using an ELISA system. The technique uses a synthetic RNA sequence containing the anchor sequence (approximately 50 nucleotides for apobec-1). After incubation with the inhibitors assayed in the presence of the enzyme in the required medium, a complementary primer of the 3' sequence of the deaminated RNA site is added, whose 5' terminal is for example labelled with one or more modified nucleotides (digoxygenated for example) under hybridisation conditions. The Reverse Transcriptase enzyme is then added and modified nucleotides, biotinilated for example (only biot-dGTP in the example illustrated in the figure). If there is deamination no incorporation takes place. In the event of inhibitor activity (no deamination) the incorporation of a biotinilated nucleotide takes place. It is therefore possible to trap the primers elongated with a biotinilated nucleotide on a support coated with streptavidine, and to expose the presence of digoxygenine with an anti-digoxygenine system followed by an ELISA reaction.

Figure 2:
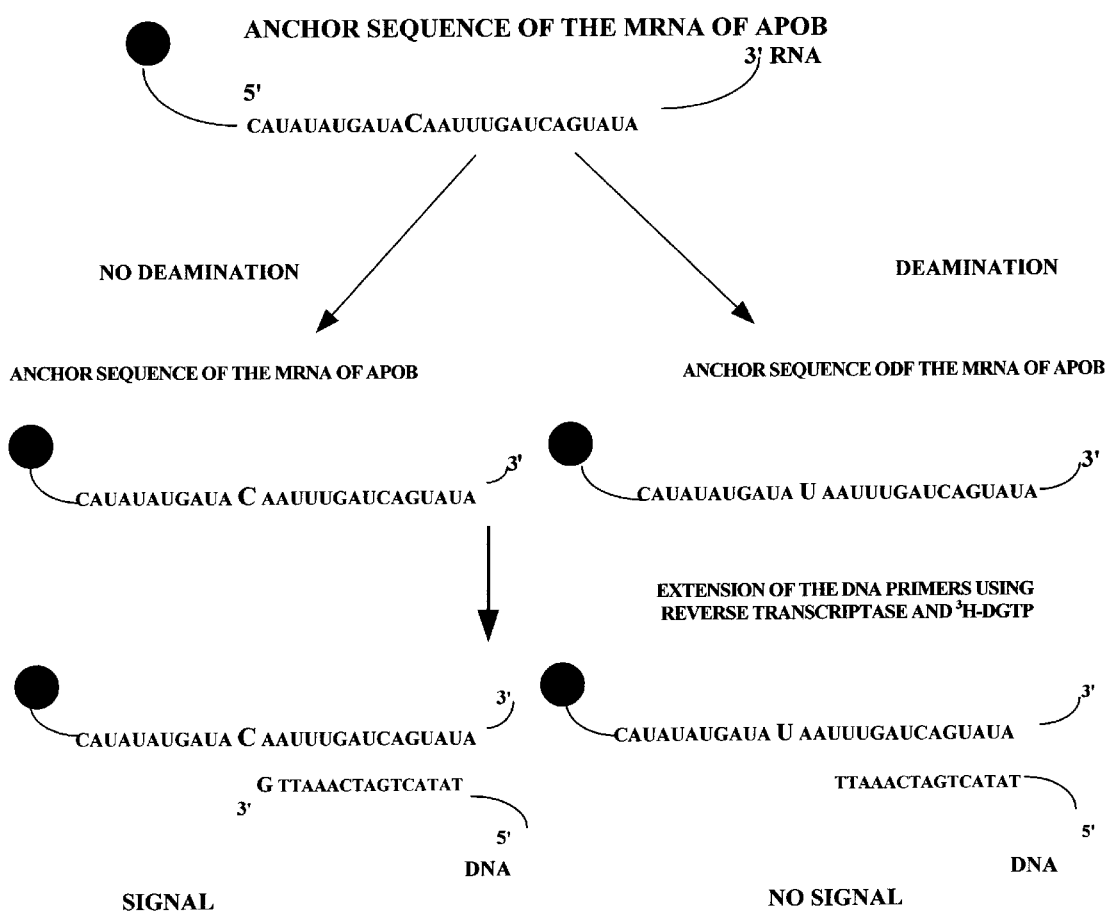

FIG. 2 Screening inhibitors of the deaminase activity of an enzyme using a technique for detacting deamination. Example of apobec-1 and a technique using the SPA® system. The technique uses a synthetic RNA sequence containing the anchor sequence (approximately 50 nucleotides for apobec-1) coupled to a SPA® pellet. After incubation with the inhibitors assayed in the presence of the enzyme in the required medium, a complementary primer of the 3' sequence of the deaminated RNA site is added under hybridisation conditions. The reverse Transcriptase enzyme is then added and radiolabelled nucleotides (only HGTP in the example of illustrated in the figure). In the event of deamination, no incorporation takes place and the detected signal is indistinguishable from background noise. In the event of inhibitor activity (no deamination), the incorporation of a radiolabelled nucleotide takes place and a signal is detected.

EXAMPLES

Example 1

Technique for screening molecules likely to inhibit the deaminase activity of apobec-1 using a staining ELISA exposure system.

The example uses a synthetic RNA sequence containing the anchor sequence of apobec-1 (approximately 50 nucleotides (Shah R R et al (1991) J. Biol. Chem. 16301–16304, Davies M S et al (1989) J. Biol. Chem. 13395–13398) placed in a 96-well dish. After incubation with the inhibitors assayed in the presence of the enzyme in the required medium, a complementary primer of the 3' sequence of the deaminated RNA site is added, whose 5' terminal is for example previously labelled with one (or more) digoxygenated nucleotides (dig 11-dUTP, marketed by Boehringer Mannheim) under hybridisation conditions. The Reverse Transcriptase enzyme is then added and modified nucleotides, that are biotinilated for example (biot-dGTP in the example in FIG. 1) that are available commercially or can be easily produced using biotinilation kits (marketed by Sigma for example). In the event of deamination, that is to say non-inhibited activity of the apobec-1 enzyme, no incorporation of the biotinilated nucleotide takes place. In the event of inhibitor activity (no deamination) the incorporation of a biotinilated nucleotide may take place. After this reaction, it is therefore possible to trap the primers elongated with a biotinilated nucleotide on the streptavidine-coated walls of the 96- well dish used and to remove non-extended primers by washing. Exposure of the presence of digoxygenine is the made using an anti-digoxygenine antibody followed by an ELISA reaction, for example antidig-alkaline-phosphatase exposed by reaction with nitroblue tetrazolium (NET) salts. The corresponding digoxygenine and antibody systems can be commercially obtained for example form Boehringer Mannheim.

Example 2

Technique for screening molecules likely to inhibit the deaminase activity of apobec-1 using the SPA® system.

The example uses a synthetic RNA sequence containing the anchor sequence of apobec-1 (approximately 50 nucleotides (Shah R R et al (1991) J. Biol. Chem. 16301–16304, Davies M S et al (1989) J. Biol. Chem. 13395–13398) coupled to a SPA® pellet (system marketed by Amersham) placed in a 96-well dish. After incubation with the inhibitors assayed in the presence of the enzyme in the required medium and with the required reagents, a complementary primer of the 3' sequence of the deaminated RNA site is added under hybridisation conditions (Maniatis T et al (1982) Molecular Cloning, a laboratory manual, Cold Spring Harbor, N.Y.). A Reverse Transcriptase enzyme is then added and radiolabelled nucleotides (only HGTP in the example illustrated in FIG. 2). In this case it is also possible to use HTTP in addition. In the event of deamination, that is to say normal activity of the apobec-1 enzyme, no incorporation takes place and the signal detected, due to proximity scintillation of the SPA pellets, is indistinguishable from the background noise. In the event of inhibitor activity, the deamination activity of abobec-1 is reduced, making it possible to incorporate one radiolabelled nucleotide (or two if HTTP is also used) at the 3' terminal of part of the hybridised primers. In this case, a scintillation signal can be detected which is distinguishable from background noise.

What is claimed is:

1. A method of testing a molecule for its potential at inhibiting deaminase catalytic activity of an apobec-1 enzyme, the method comprising the steps of interacting the apobec-1 enzyme with an aminated nucleic acid substrate in a presence and in an absence of the molecule and determining an inhibition effect of the molecule on the catalytic activity of the apobec-1 enzyme toward said substrate.

2. The method of claim 1, wherein said aminated nucleic acid substrate is at least a portion of an RNA encoding apo B, said portion including an endogenously deaminated site of apo B mRNA in an aminated form.

3. The method of claim 1, wherein said step of determining said inhibition effect of the molecule on the catalytic activity of the enzyme toward said substrate is effected by a colorimetrically or fluoimetrically monitorable primer extension reaction.

4. A method of testing a molecule for its potential at inhibiting apobec-1 deaminase catalytic activity, the method comprising the steps of interacting said apobec-1 with at least a portion of an RNA encoding apo B, said portion including an endogenously deaminated site of apo B mRNA in an aminated form, in a presence and in an absence of the molecule and determining an inhibition effect of the molecule on the catalytic activity of the apobec-1 toward said substrate.

5. The method of claim 4, wherein said step of determining said inhibition effect of the molecule on the catalytic activity of the apobec-1 toward said substrate is effected by a colorimetrically or fluoimetrically monitorable primer extension reaction.

6. A method of testing a molecule for its potential at inhibiting deaminase catalytic activity, the method comprising the steps of interacting an enzyme having said deaminase catalytic activity with an aminated nucleic acid substrate in a presence and in an absence of the molecule and determining an inhibition effect of the molecule on the catalytic activity of the enzyme toward said substrate, wherein said aminated nucleic acid substrate is at least a portion of an RNA encoding apo B, said portion including an endogenously deaminated site of apo B mRNA in an aminated form.

7. The method of claim 6, wherein said step of determining said inhibition effect of the molecule on the catalytic activity of the enzyme toward said substrate is effected by a colorimetrically of fluoimetrically monitorable primer extension reaction.

* * * * *